US00PP28135P3

(12) United States Plant Patent
Olesen

(10) Patent No.: US PP28,135 P3
(45) Date of Patent: Jun. 27, 2017

(54) GROUND COVER ROSE PLANT NAMED 'POULTC022'

(50) Latin Name: ***Rosa* hybrid**
Varietal Denomination: Poultc022

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 14/756,250

(22) Filed: Aug. 20, 2015

(65) Prior Publication Data

US 2017/0055384 P1 Feb. 23, 2017

(51) Int. Cl.
*A01H 5/02* (2006.01)

(52) U.S. Cl.
USPC ..... Plt./101

(58) Field of Classification Search
USPC ..... Plt./101
CPC ..... A01H 5/0222
See application file for complete search history.

(56) References Cited

PUBLICATIONS http://www.poulsenroser.dk/media/73809/TOWNE-COUNTRY-2013_LR_Poulsen-Roser.pdf; 2012, 1 page.*

* cited by examiner

*Primary Examiner* — Kent L Bell

(57) ABSTRACT

A new garden rose plant of the ground cover class which has abundant, apricot flowers and attractive foliage. This new and distinct variety has shown to be uniform and stable in the resulting generations from asexual propagation.

2 Drawing Sheets

Botanical designation: *Rosa* hybrid.
Variety denomination: 'Poultc022'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2006 and the resulting seeds were planted in a controlled environment in Fredensborg, Denmark. The new variety, named 'Poultc022', originated as a single seedling from the stated cross.

The new variety may be distinguished from its male pollen parent and female seed parent primarily by the following characteristics. The female seed parent has flowers which are Yellow-Orange Group 19B, while the new variety has flowers which are Orange Group 24B. The male pollen parent has orange red flowers.

The objective of the hybridization of this rose variety was to create a new and distinct variety for garden use with unique qualities, such as:

1. Uniform and abundant apricot flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poultc022' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poultc022' was selected in the spring of 2007 by the inventor as a single plant from the progeny of the aforementioned hybridization.

Asexual reproduction of 'Poultc022' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poultc022' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poultc022'.

Specifically illustrated in FIG. 1 of the drawings are open flowers, flower petals detached, leaves, reproductive flower parts, bare stem and sepals detached.

Figure 1:
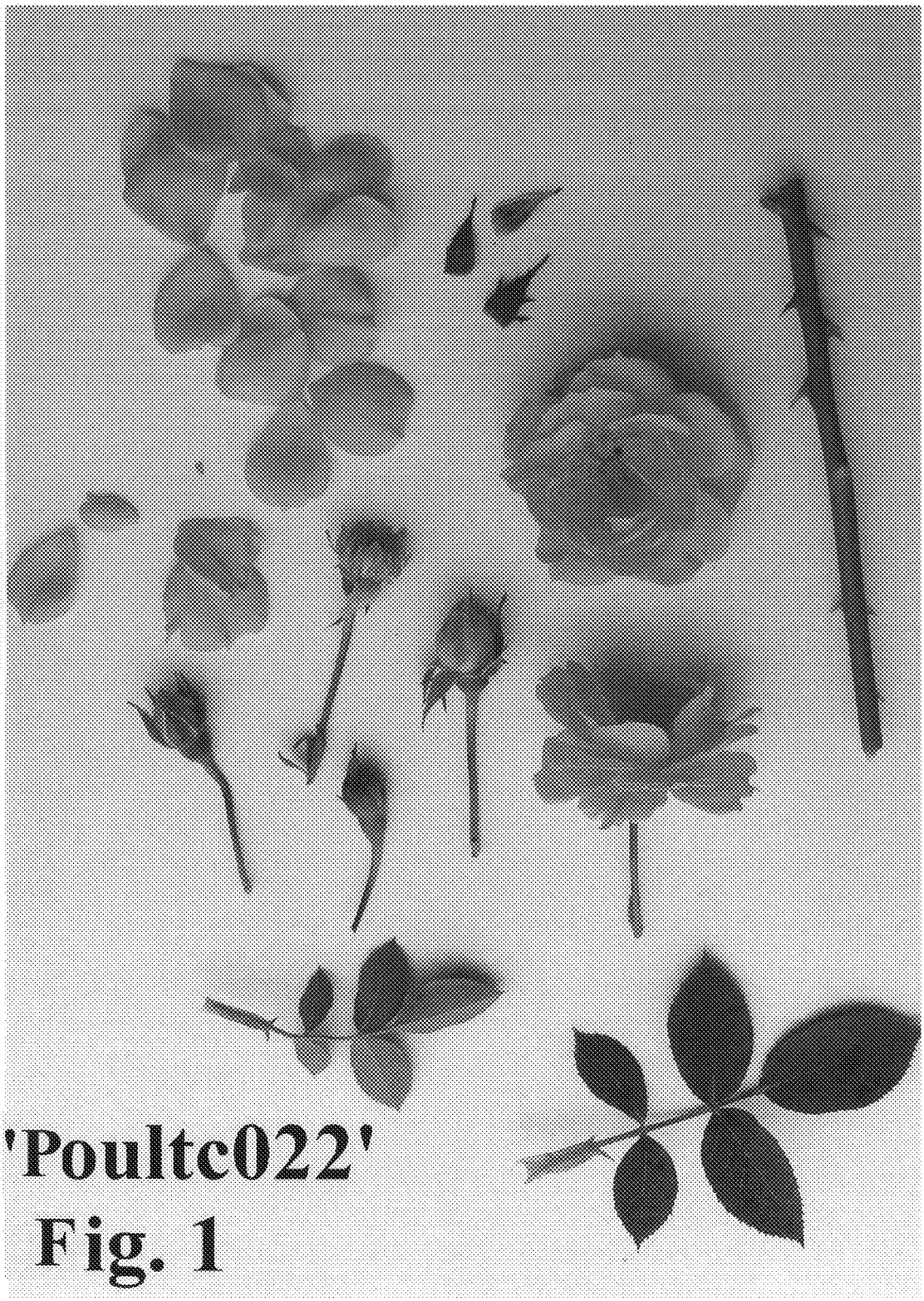
Figure 2:
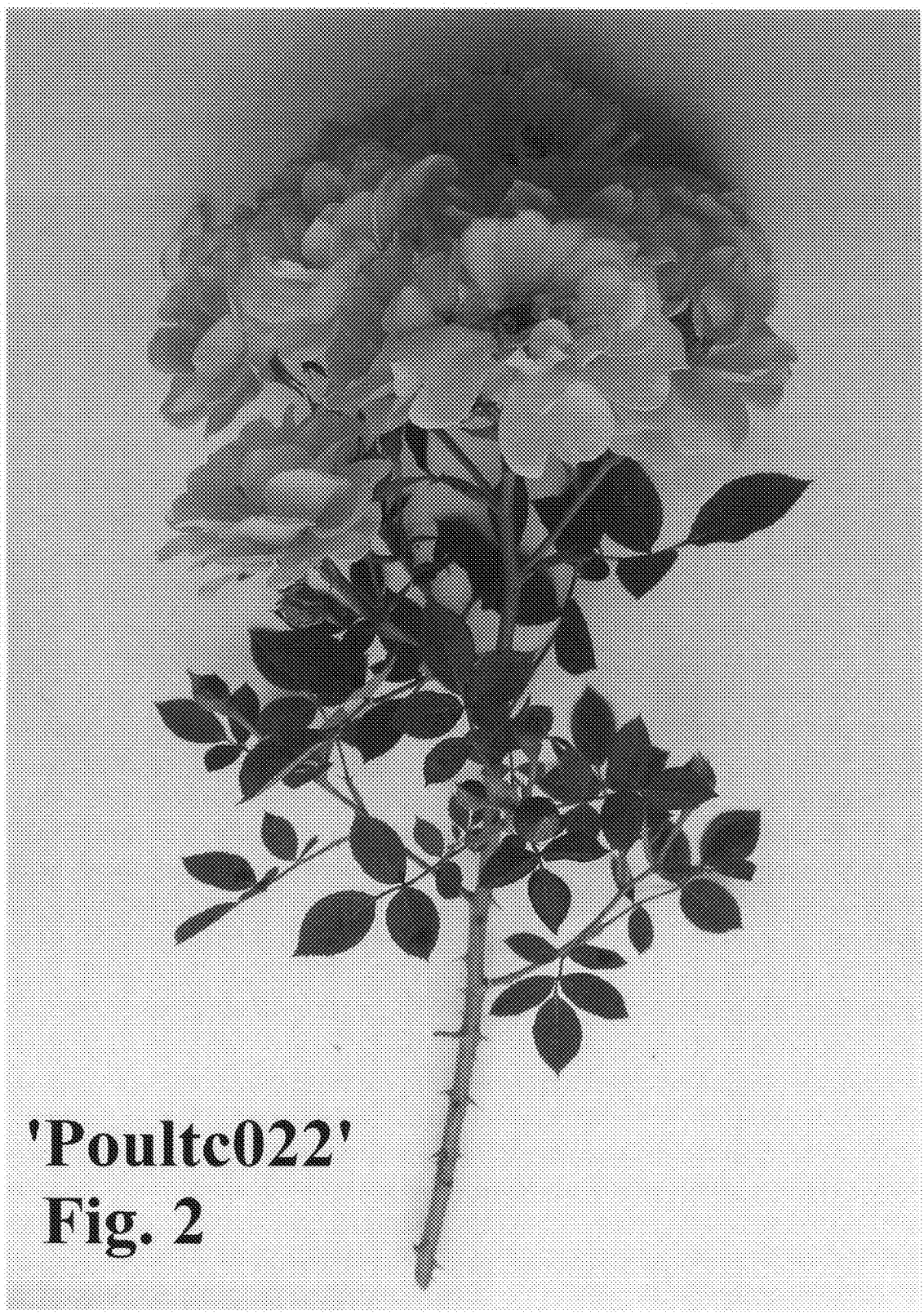

Specifically illustrated in FIG. 2 is a cluster of open flowers on a branch.

Plants shown are 2 years of age.

DETAILED DESCRIPTION OF THE VARIETY

The following is a description of 'Poultc022',as observed in its growth in a field nursery in Marion County, Oreg.

Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulbambe', described and illustrated in U.S. Plant Pat. No. 13,292 are compared to 'Poultc022' in the chart entitled Comparison with a comparative cultivar 'Poulbambe'.

Comparison with a Comparative Cultivar 'Poulbambe'

CHART 1

| | 'Poultc022' | 'Poulbambe' |
|---|---|---|
| Petal Count | 25 | 18-22 |
| Flower Diameter | 45 mm | 60 mm |
| General Tonality of Flower Color | Orange Group 24B fading to Yellow-Orange Group 23C | Yellow-Orange Group 19A |

Flower and Flower Bud

Blooming habit: Continuous.

Flower bud:

*Size.*—Upon opening, 20 mm in length from base of receptacle to end of bud. Bud diameter is 9 mm.

*Bud form.*—Urceolate.

*Bud color.*—As sepals divide petals are Yellow Group 8A and Orange Group 26B.

*Sepal inner surface.*—Color: Yellow-Green Group 145C. Surface: Lightly pubescent.

*Sepal outer surface.*—Color: Yellow-Green Group 144A with intonations of Greyed-Red Group 183A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—15 mm long, 5 mm wide.

*Receptacle.*—Texture: Smooth. Size: 5 mm in height, 6 mm wide. Color: Yellow-Green Group 144A with intonations of Greyed-Red Group 183A. Shape: Campanulate.

*Pedicel.*—Surface: Smooth. Length: 25 mm. Diameter: 1.5 mm on average. Color: Yellow-Green Group 144A with intonations of Greyed-Orange Group 175A. Strength: Moderate.

*Peduncle.*—Length: 4 to 9 cm. Diameter: About 3 mm. Color: Yellow-Green Group 144A. Texture: Smooth.

Flower bud development: Flower buds are borne in panicles of about 35 flower buds per stem.

Flower bloom:

*Fragrance.*—Light floral.

*Duration.*—The blooms have a duration on the plant of approximately 10 days. Petals fall cleanly away from plant after flowers have fully matured.

*Size.*—Flower diameter is 45 mm when open. Flower depth is 20 mm.

*Flower shape.*—Open cup.

*Shape of flower, side view.*—The upper portion is convex. The lower portion is concave.

Petalage: Under normal conditions, flowers have 25 petals total, 3 to 4 of which are petaloids.

General tonality of flower: Open flowers are Orange Group 24B fading to Yellow-Orange Group 23C.

Petal color:

*Upon opening.*—Upper surface: Orange Group 24B with a petal spot which is Yellow Group 9B. Lower surface: Orange Group 25C with a petal spot which is Yellow Group 9B.

*After opening.*—Upper surface: Yellow-Orange Group 19B with streaks of Red Group 39B. Lower surface: Yellow-Orange Group 19B blended with Orange Group 27B.

Petals:

*Petal reflex.*—Somewhat reflexed.

*Margin.*—Slight point at the apex.

*Shape.*—Generally elliptical. Apex shape: Rounded. Base shape: Acute.

*Size.*—25 mm (l)×20 mm (w).

*Texture.*—Smooth.

*Thickness.*—Average.

Petaloids:

*Size.*—16 mm (l) by 7 mm (w).

*Quantity.*—3 to 4.

*Shape.*—Elliptical.

*Color.*—Upper surface is Orange Group 24B with a petal spot which is Yellow Group 9B. Lower surface is Orange Group 25C with a petal spot which is Yellow Group 9B.

Reproductive flower parts:

*Pollen.*—None observed.

*Anthers.*—Size: 2 mm in length. Color: Yellow-Orange Group 20B. Quantity: 35 on average.

*Filaments.*—Color: Yellow-Orange Group 22C. Length: 4 mm.

*Pistils.*—Length: 2 to 3 mm. Quantity: 20 on average.

*Stigmas.*—Color: Greyed-Yellow Group 162C.

*Styles.*—Color: Red-Purple Group 63C.

*Location of stigmas.*—Inferior in location relative to the length of the filaments and the height of the anthers.

*Hips.*—None Observed.

Plant

Plant growth: Upright, bushy. Plants are 55 cm in height, and 65 cm wide.

Stems:

*Color.*—Juvenile growth: Yellow-Green Group 144B. Mature growth: Yellow-Green Group 144A.

*Length.*—On average, canes are 25 cm from the base of the plant to the flowering portion.

*Diameter.*—About 8 mm.

*Internodes.*—On mature canes about 30 mm between nodes.

*Surface texture.*—Young wood: Smooth. Older wood: Smooth.

Long prickles:

*Incidence.*—6 to 8 prickles per 10 cm of stem.

*Size.*—Average length of prickles on mature stems is 5 mm.

*Shape.*—Upper portion is convex. Lower portion is concave.

*Color.*—Juvenile prickles: Greyed-Red Group 180B. Mature prickles: Greyed-Orange Group 164B.

Plant foliage:

*Compound leaf.*—85 mm (l)×55 (w).

*Quantity.*—3 leaves per 10 cm of stem on average.

*Color of juvenile foliage*.—Upper side: Yellow-Green Group 144A. Lower side: Yellow-Green Group 144B.

*Color of mature foliage*.—Upper side: Yellow-Green Group 146A. Lower side: Yellow-Green Group 146B.

Plant leaves and leaflets:

*Stipules*.—Size: 15 mm long, 7 mm wide. Quantity: 2 per compound leaf. Shape: Linear, slightly broad based with outward extending apices. Margins: Finely serrated. Color: Yellow-Green Group 144B.

*Petiole*.—Length: 25 mm. Diameter: 1 mm.

*Upper surface*.—Color: Yellow-Green Group 144B.

*Lower surface*.—Color: Yellow-Green Group 144B.

*Rachis*.—Length: 25 mm.

*Upper surface*.—Color: Yellow-Green Group 144B.

*Lower surface*.—Color: Yellow-Green Group 144B.

*Leaflet*.—Quantity: Normally 5 leaflets. Margins: Serrated. Size: On average terminal leaflets are 35 mm long, 20 mm wide. Shape: Generally elliptical. Base: Rounded. Apex: Cuspidate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the ground cover rose class named 'Poultc022', substantially as illustrated and described herein, due to its abundant apricot flowers, disease resistance, and extended period of bloom.

* * * * *

'Poultc022'

'Poultc022'